United States Patent [19]

Björk et al.

[11] Patent Number: 4,647,207
[45] Date of Patent: Mar. 3, 1987

[54] ELLIPSOMETRIC METHOD AND APPARATUS

[75] Inventors: Nils A. N. Björk, Täby; Erland T. Sandström, Mölndal; Johan E. Stenberg; Lars B. Stiblert, both of Göteborg, all of Sweden

[73] Assignee: Sagax Instrument AB, Sundbyberg, Sweden

[21] Appl. No.: 737,534

[22] Filed: May 24, 1985

[30] Foreign Application Priority Data

May 24, 1984 [DE] Fed. Rep. of Germany ....... 3419463

[51] Int. Cl.⁴ ........................................... G01N 21/21
[52] U.S. Cl. ..................................... 356/369; 356/243
[58] Field of Search ............... 356/364, 367, 369, 243, 356/244

[56] References Cited

U.S. PATENT DOCUMENTS 4,210,401 7/1980 Batten ............................ 356/244 X
4,332,476 6/1982 Stenberg et al. .................... 356/369
4,355,903 10/1982 Sandercock ..................... 356/243 X Primary Examiner—Davis L. Willis
Assistant Examiner—Matthew W. Koren
Attorney, Agent, or Firm—Fleit, Jacobson, Cohn & Price

[57] ABSTRACT

An ellipsometric method and apparatus for studying physical properties of a testpiece provides that during the measuring operation the angular positions of a polarizing means and an analyzing means disposed upstream and downstream of the testpiece remain fixed. Two or more discrete, mutually different predetermined states of polarization of the radiation employed are produced between the polarizing means and the testpiece and/or between the testpiece and the analyzing means, by polarization modulating elements which are disposed in the path of the radiation. In each discrete state of polarization, the intensity of the radiation which is polarized in the analyzer is measured and evaluated for determining the polarization properties of the testpiece in a computer.

25 Claims, 1 Drawing Figure

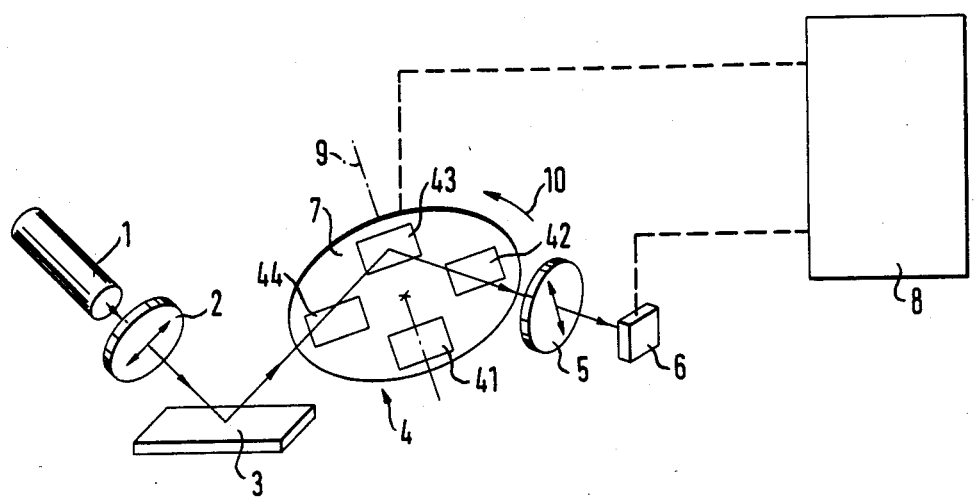

ELLIPSOMETRIC METHOD AND APPARATUS

BACKGROUND OF THE INVENTION

The invention relates generally to an ellipsometric method for studying physical properties of a sample or testpiece, and an apparatus for carrying out the method. The physical properties of the testpiece, which are the subject of study in accordance with the method and the apparatus, include the properties of a surface of the testpiece or one or more surface layers or films on the testpiece.

The term ellipsometry is used as a collective term for denoting various methods for studying the physical properties of testpieces by means of their properties of changing the polarisation of a polarised light beam. In principle, a beam with a known state of polarisation is reflected at or transmitted through the testpiece. After reflection at the testpiece or after the light has passed through the testpiece, the physical properties of the testpiece can be ascertained from the change in polarisation, using optical calculations.

In reflection ellipsometry, the testpiece has a reflective surface on which the light beam impinges, with an oblique angle of incidence. The ellipsometric data obtained can be used for ascertaining the refractive index and the extinction coefficient of the surface material of the testpiece. If the testpiece is covered with a dielectric film, it is possible to determine the thickness and the refractive index of the film. Reflection ellipsometry is the most sensitive and most accurate method for measuring such films or layers.

Instead of using a reflected beam, it is also possible to analyse the light beam which is transmitted through the testpiece. That method is referred to as transmission ellipsometry.

The same procedure which is used for measuring the change in polarisation in transmission ellipsometry can also be employed for studying bulk properties of transparent materials, for example the birefringence of crystals or optical rotation of a sugar solution. The latter is conventionally referred to as polarimetry, but it falls within the general term of ellipsometry.

For the sake of simplicity hereinafter, reference will primarily be made to reflection ellipsometry but it should be appreciated that, unless stated otherwise, the information and procedures set forth also apply to transmission ellipsometry and polarimetry as referred to above.

In ellipsometry, the physical parameters of the testpiece, which are the aspects of interest, simultaneously affect the relative intensity and the phase delay of the two polarisation components of the light beam. As external influences affect the two polarisation components to the same degree, ellipsometry is very insensitive with respect to such external influences. That also explains the extremely high degree of accuracy of ellipsometric measuring methods in conventional laboratory equipment.

Ellipsometry is a highly developed art, and there are many publications relating thereto, for example R. N. A. Azzam and N. M. Bashara 'Ellipsometry and Polarised Light', North Holland Publishing Co, New York, 1977, disclosing various aspects of ellipsometry. In regard to ellipsometric methods, a distinction is made in particular in regard to the instrument used (also referred to as the ellipsometer) and the procedures used for extracting and interpreting the measurement data.

An ellipsometer essentially comprises a light source for emitting polarised light, a testpiece and an analyser which analyses polarisation of the light after it has been reflected at the testpiece or after it has been transmitted through the testpiece. More particularly, an ellipsometer comprises a light source and a detector together with two polarisers, one of which is disposed near the light source and is conventionally referred to as the polariser, while the other is disposed in the vicinity of the analysing means and is generally referred to as the analyser. The testpiece is disposed between the polariser and the analyser, and the assembly may include one or two devices for altering or modifying the polarisation of the light, referred to as polarisation modifying devices or polarisation modulating devices. The polarisation modulating devices may be polarisers which produce a partial polarisation effect, or birefringent devices (which are referred to as compensators), or optical rotators and/or geometrical rotators. If for example the polariser is rotated relative to the testpiece, that is a geometrical rotation. The differences between the individual kinds of ellipsometers arise out of the choice of the device used for modifying the state of polarisation. The basic construction of an ellipsometer with a compensator ($\lambda/4$ plate) as the means for modifying the state of polarisation of the radiation is described for example in Journal of Physics E; Scientific instruments, volume 6, No. 5, May 1973, by W. E. J. Neal et al; 'Ellipsometry and its applications to surface examination', pages 409 to 413, in particular page 410.

By virtue of the particular design construction selected, ellipsometers have different properties, for example in regard to accuracy, high measuring speed and suitability for operation with multiple wavelengths.

Because of the non-directional nature of optical laws, the sequence in which the optical components are disposed may be interchanged, between the two polarisers. The mode of operation of the overall assembly then remains the same although the actual condition of the optical components must be taken into consideration when analysing the measurement data.

Ellipsometric methods can be essentially divided into photometric ellipsometry and null ellipsometry. In null ellipsometry, the change in the state of polarisation which is caused by the testpiece is compensated by suitable adjustment of the polarisation modulating device so that the light beam is extinguished by the analyser. Adjustment to a minimum level of received intensity may be effected either manually or automatically. The measurement result is then the position of the polarisation modulating device, upon extinction of the light beam. Such a method is disclosed for example in published European patent application No. 80 101993.6 (publication No. 0 019 088).

In photometric ellipsometry, the devices for altering the state of polarisation are varied in a predetermined manner and the intensity of light reaching the detector is measured for each setting of the polarisation modulating device. The ellipsometric data for the testpiece are then calculated using mathematical models for the respective instrument.

Adjustment or setting of the polarisation modulating device may be effected by rotatable modulator members, wherein one or both polarisation modulating devices is or are continuously changed by rotation of the optical components thereof, which are of a rotationally asymmetrical construction, thereby continuously changing the state of polarisation of the light beam. In that connection, the rotary movement of the polariser or a compensator is frequently effected at a constant speed about an axis of rotation which is parallel to the path of the light beam and the waveform of the received signal is measured during that procedure.

Another photometric ellipsometric method provides using one or more electro-optical polarisation modulating devices for varying the state of polarisation, the modulation properties of such devices being suitably controlled for that purpose and the waveform thus being measured.

Also known are ellipsometric beam division methods wherein the beam, after being reflected at the testpiece or after passing through the testpiece, is split into two or more light beams, with the split beams being measured by different detectors. Different polarisation modulating devices are provided for the split beams. The properties of the testpiece in question can be ascertained on the basis of knowledge of the properties of the polarisation modulating devices and the measured intensities.

The null ellipsometric method requires a detector which is sensitive to the radiation, but not a detector which provides for quantitative measurement, in other words, the naked eye of the operator is sufficient. Although a relatively high degree of accuracy is achieved in that context, the mode of operation is slow. The degree of accuracy depends on the accuracy with which the settings of the polarisation modulating device can be read off. In many cases, this involves optical elements which are rotated by mechanical means. Photometric ellipsometric methods depend for their accuracy on the measuring accuracy of the detector which receives the light intensity. In the case of components of the ellipsometer which are adjustable by a rotary movement, it is necessary to ascertain and measure the angular position of those components as well as the received light intensity, to a very high degree of accuracy. As the light intensities are measured at different times, fluctuations in the light source will have a detrimental effect on the measurement result. In the case of the beam division method, although variations in the intensity of the light source do not have a disadvantageous effect, changes in sensitivity between the individual detectors and receivers will adversely affect the measurement result.

SUMMARY OF THE INVENTION

An object of the present invention is to provide a method of studying the physical properties of a testpiece or a surface or a surface layer of a testpiece, which can be used for a wide range of different ellipsometrical measurement operations.

Another aspect of the present invention is to provide an ellipsometer apparatus which, with the same electronic and optical construction, permits ellipsometrical measurement operations to be carried out over a wide range of types.

A further object of the present invention is to provide a novel ellipsometer apparatus which permits accurate measurement to be made relatively quickly.

Still another object of the present invention is to provide an ellipsometer apparatus which permits high levels of accuracy to be achieved, more particularly in regard to the measurement of thin films.

According to the present invention, those and other objects are achieved by an ellipsometric method for studying physical properties of a testpiece or a surface layer or layers thereon, wherein electromagnetic radiation is reflected or transmitted by the testpiece after having been subjected to a first polarisation effect at first polarising means. Downstream of the testpiece, the radiation is subjected to a second polarisation effect in a second polarising means and the radiation is then measured and interpreted. The state of polarisation of the radiation is altered between the first polarising means and the testpiece or between the testpiece and the second polarising means. During the measuring operation, at the testpiece, the angular settings of the two polarising means remain fixed, while during the measuring operation, between the first polarising means and the testpiece and/or between the testpiece and the second polarising means, by stepwise alteration, two or more discrete mutually different predetermined states of polarisation of the radiation are produced by means of reflection at reflecting surfaces having different optical properties, with an angle of incidence $>0°$ and $<90°$, and, in regard to each discrete state of polarisation, the intensity of the radiation polarised in the second polarising means is measured and evaluated or interpreted for determining the polarisation properties of the testpiece or surface thereof, as for example in a computer.

In an ellipsometer apparatus for carrying out a method according to the principles of the present invention, disposed between a polariser and an analyser is a means for disposing a testpiece, in the path of the radiation between the polariser and the analyser. Disposed upstream of the polariser is a light source while a detector is disposed downstream of the analyser for receiving light coming therefrom. A polarisation modulating device is provided for varying the state of polarisation of the radiation between the polariser and the testpiece and/or the testpiece and the analyser. The polarisation modulating device comprises a plurality of polarisation modulating elements with different predetermined optical properties which are stepped from each other, being disposed at positions which differ in respect of space and which are successively movable into the path of the radiation, with an angle of incidence of $>0°$ and $<90°$, the polarisation modulating elements being formed as reflecting surfaces, each of which is covered with a homogeneous optically isotropic medium. The layer thicknesses and/or refractive index of the optically isotropic media of the individual polarisation modulating elements differ from each other.

It will be seen therefore that the invention provides a novel photometric ellipsometric method and a novel photometric ellipsometer, wherein a polarisation modulating device is altered in discrete predetermined steps in regard to its properties which influence the polarisation of the light beam, in the form of reflecting surfaces which have different optical properties and on to which the radiation impinges at an acute angle, in particular at an angle of incidence of from 45° to 80°, with measurements being made in respect of the respective intensities which correspond to the discrete step values and which are received by a detector. The polarisation properties of the testpiece are calculated from the above-mentioned received intensities and on the basis of knowledge of the discrete adjustment values of the polarisation modulating device, which differ from each other in a stepwise fashion.

The ellipsometer according to the present invention employs two or more polarisation modulating elements, for use with different predetermined properties, which are discrete relative to each other, for influencing the polarisation of the elliptical light. The polarisation modulating elements are disposed at positions in the polarisation modulating device which differ in terms of space and are successively moved into the path of the light beam. The polarisation modulating elements are such that, by means thereof, with the polariser and the analyser fixed in position, during the measuring operation at a testpiece, different levels of intensity, in a stepped relationship, are received and measured.

The polarisation modulating elements are reflecting surfaces which are coated with a homogeously optically isotropic medium, the layer thicknesses and/or refractive index of the isotropic media of the individual polarisation modulating elements differing from each other. One or more layers may be provided on each of the reflecting surfaces. The polarisation modulating elements may be disposed on a rotatable carrier which moves the individual polarisation modulating elements into the path of the light beam. In that connection, the axis of rotary movement is normal to the reflecting surfaces of the polarisation modulating elements.

However, instead of the rotary movement for bringing the individual polarisation modulator elements into the path of the light beam, it is also possible to move the said elements into the path of the light beam by displacement of polarisation modulating elements which are disposed in a row, or by means of a reciprocating movement thereof.

Unlike the conventional photometric method and photometric ellipsometers, the invention provides for a stepwise change in the state of polarisation of the polarised light between the polariser and the analyser. The respective discrete state of polarisation is maintained as long as the polarisation modulating element in question is in the path of the beam of polarised light. The level of intensity associated with each polarisation modulating element is measured. In that way, the polarisation properties of the testpiece may be ascertained from the known values or settings of the polarisation modulating elements and the associated levels of intensity. In turn, from the testpiece polarisation properties, it is possible to determine in particular the refractive index and the extinction coefficient of surface layers of the testpiece. If the state of polarisation is altered, when the light passes through the testpiece, it is possible to determine properties of the transparent testpiece material, for example birefringent properties.

The polarisation modulating elements may comprise polished silicon, with the polished surfaces bearing dielectric films of different thicknesses and/or refractive indexes. In the measuring operation, the polarised light with which the testpiece is investigated is reflected at the polished surfaces. The polarisation properties of an isotropic surface of that kind, which operates in a similar fashion to a compensator, only depend on the angle of incidence and the wavelength of the light with which the testpiece is being investigated. Neither the angle of incidence nor the wavelength of the light change while a surface of a polarisation modulating element is being exposed to the light.

Besides the broad range of possible uses in relation to different ellipsometrical measuring processes, without alteration in the optical or electronic set-up, the invention also has further advantages, as set out below. When using four different polarisation modulating elements, in particular those which have reflecting surfaces, it is possible to perform full Stokes-vector ellipsometry. The Stokes-vector of the light beam coming from the testpiece may be ascertained from the measurement of the four levels of intensity I1 through I4, by means of the following matrix equation:

$$\overline{S} = \overline{I} M$$

The matrix $M$ is calculated from the known properties of the four polarisation modulating elements. In order for M to exist, the matrix M must have a determinant which differs from zero. That condition can be easily fulfilled by suitably selecting the polarisation modulating elements, in particular the surface layers on the reflecting surfaces of the polarisation modulating elements which operate like compensators.

A light beam may be described in various ways. For a monochromatic polarised light beam, the following equation applies as the specification of the instantaneous electrical field vector:

$$\overline{E} = (E_x \hat{x} + E_y \hat{y}) e^{-j(wt - kz + \theta)}$$

In the foregoing equation, $E_x$ and $E_y$ denote complex amplitude values, x and y are cartesian base vectors in the X- and Y-directions, z is the direction of propagation, w is the angular frequency, k is a propagation constant and $\theta$ is a constant phase angle.

The total intensity may be expressed by the following:

$$I = |E_x|^2 + |E_y|^2$$

Polarisation may be represented by the complex quantity:

$$\rho = E_x / E_y$$

The phase angle $\theta$ is indeterminate and cannot be measured for an individual light beam.

In the general case of finite band width and light which is not fully polarised, account should also be given to a parameter P which gives the degree of polarisation, that is to say, the proportion of the intensity of the polarised component to the total intensity. That radiation may be described in physics terms by the Stokes-vector:

$$\overline{S} = (I, S_1, S_2, S_3)$$

The four vector elements give the result of four different intensity measurements which are carried out on the light beam. The Stokes-vector can be transformed to I, $\rho$ and P. The ellipsometer measures the change in $\rho$ or $|\rho|$ which is caused by the testpiece. The parameter I may also be determined in photometric ellipsometers. Full Stokes-vector ellipsometers give the full Stokes-vector S or I, $\rho$ and P.

Conversion of a change in $\rho$ into values of thickness and refractive index is effected by comparison with a table of values which is calculated from optical theory and held in store, in an on-line digital computer.

In that connection, the instrument uses all items of information which are available from the light beam, namely the intensity I, the complex quantity $\rho$ and the degree of polarisation P. In many situations of ellipsometry use, the degree of polarisation is unity, and the measurement value in respect of the degree of polarisation can be used for checking the instrument in ascertaining errors and in ascertaining inconsistencies in regard to measurement, for example lack of homogeneity of the testpieces over the surface being investigated can be detected. In other situations of use, measurement of the degree of polarisation P makes it possible to study unknown surfaces, for example rough surfaces.

If a given geometry in respect of the arrangement of the optical components of the ellipsometer relative to each other is used such that the light impinges with the same angle of incidence on the surfaces of the polarisation modulating elements which act as compensators, and on the testpiece, and the planes of incidence are normal to each other, it is possible, by suitable setting of the polariser and the analyser, to achieve a condition wherein the detector does not receive any light when the surface of the polarisation modulating element, which acts as the compensator, is the same as the surface of the testpiece. Such a condition is also achieved with the null ellipsometer which is disclosed in above-mentioned published European patent application No. 80 102993.6 (publication No. 0 019 088). There is then no need for mathematically determining the surface properties because the physical parameters which are of interest in this connection are given directly by the polarisation modulating element which serves as a reference surface.

If the same geometry is used with two or more polarisation modulating surfaces, in particular with coated reflecting surfaces with different thicknesses of layers thereon, and if the surfaces of the polarisation modulating elements and the testpiece are of the same type, it is easily possible to determine the thickness of the layer or film on the testpiece, from the measured levels of intensity. The mathematical involvement in that connection is significantly less than was conventionally the case hitherto. That advantage is enjoyed in particular when the surfaces of the polarisation modulating elements and the testpiece lie within a relatively narrow range of thicknesses. In that case, the received intensity $I_d$ is in accordance with the following formula:

$$I_d = I_1 (d_t - d_c)^2 + I_0$$

wherein $d_t$ denotes the unknown thickness of the layer on the testpiece, $d_c$ denotes the thickness of the layer on the reflecting surface which acts as a compensator, and $I_1$ and $I_0$ are unknown instrument factors. The unknown constants can be ascertained from three pairs of values in respect of $I_d$ and $d_c$, without requiring the computational complexity of conventional full ellipsometry for that purpose.

With a wider range of thicknesses, the received intensity is given by the following formula, which includes a correction factor $c(d_c)$ in order to take account of changes in the total reflected intensity:

$$I_d = I_1 c(d_c)(d_t - d_c)^2 + I_0$$

A large number of sources of error vanish if the testpiece and the polarisation modulating elements are almost identical, with the specific geometry set forth hereinbefore, particularly when the polarisation modulating elements used are coated reflecting surfaces which act in a similar manner to a compensator and which are almost identical to the testpiece surface to be studied. It is then possible to carry out measurement operations with a very high degree of accuracy. That is a matter of major importance when measuring very thin films, wherein the thickness of the thin films to be measured may be less than the thickness of the layer of the homogeneous optically isotropic medium on the reflecting surface of the respective polarisation modulating element. The thickness of the layer on the testpiece can then be ascertained by interpolation from the different measured levels of intensity.

With the null ellipsometric method referred to above, it is difficult to achieve the desired degree of accuracy when measuring extremely thin films. That is because thin films of that kind, of the order of magnitude of a few Ångström, are not sufficiently stable to be used as reference surfaces, for example in the null ellipsometric method disclosed in above-mentioned published European patent application No. 80 101 993.6 (publication No. 0 019 088). With the present invention however, the thicknesses of the layers in respect of the respective homogeneous optically isotropic media on the reflecting surfaces of the polarisation modulating elements may be of such a thickness that they form stable films, in which respect, on the basis of the above-mentioned interpolation process, when interpreting the various measured levels of intensity, there does not have to be any equivalence or identity between the testpiece surface and the surface of the polarisation modulating element.

The photometric ellipsometer which is used for carrying out the method in accordance with the present invention is of a simpler construction than a conventional ellipsometer. It uses only one detector and accordingly only one amplifier for the detector signal. There is no need for precise control of the angular positioning of rotary components. Furthermore, the ellipsometer does not require any electro-optically modulated elements.

The properties of the polarisation modulator which are used in the present invention are constant in a stepwise manner. Accordingly, interation of the detector current during a respective 'constant period' makes it possible to reduce detector noise and there is no need to provide for fast sampling and corresponding data conversion.

It should be noted here, as will be seen also hereinafter, that there is no need to use either fully polarised or monochromatic light. That further enhances the flexibility of use of the ellipsometer. In addition, the present invention provides a very high degree of flexibility in regard to the selection of a suitable light source. The light source can be adjusted to different wavelengths and can be used in conjunction with wavelength scanning. The light source may also be completely free of transmission optics, for difficult spectral regions such as for example vacuum UV or far IR. It is possible to use single-reflection Brewster angle polarisation as the polarising effect is not critical and the polariser and analyser are not displaced during the measuring operation.

The invariability of the light received by the detector, over given finite periods of time, affords the possibility of replacing the detector by a parallel-detection spectrometer. That spectrometer disperses different wavelengths of the light to a spectrum and detects that spectrum with a photodiode array or a charge-coupled device (CCD). In that way, it is possible simultaneously to collect and detect ellipsometric data for a large number of wavelengths. The range of use of ellipsometry is considerably enhanced by multi-wavelength ellipsometry. Thick films can be measured thereby, without giving rise to difficulties due to the ambiguities in measuring thickness, which occur with monochromatic ellipsometers. Refractive indices can be measured for all thicknesses, which is not possible when using monochromatic ellipsometers. Finally, multi-layer structures can be resolved and determined from the multi-wave measuring data.

BRIEF DESCRIPTION OF THE DRAWING

The single FIGURE of drawing shows an embodiment of the present invention.

DESCRIPTION OF THE PREFERRED EMBODIMENT

Referring to the drawing, shown therein is an assembly wherein a testpiece or sample 3 is irradiated at its surface with light which is emitted by a light source 1 and which is polarised by a first polarising means 2 which is thus disposed between the light source 1 and the testpiece 3.

The beam which is reflected at the surface of the testpiece and which is elliptically polarised is directed on to a polarisation modifying or modulating device as indicated generally at 4, comprising four different polarisation modifying or modulating elements 41, 42, 43 and 44. The polarisation modulating elements 41, 42, 43 and 44 are in the form of reflecting surfaces which are coated with a dielectric film. It is also possible for a plurality of films to be provided on each reflecting surface. The modulating elements may be polished silicon foils which have thereon a surface coating formed by a dielectric film, for example of silicon dioxide. The polaristion modulating elements 41, 42, 43 and 44 are disposed on a carrier 7 which is rotatable about an axis as indicated at 9. The axis 9 extends normal to the reflecting surfaces of the polarisation modulating elements 41, 42, 43, and 44.

During the measuring procedure, the polarisation modulating elements are successively moved into the path of the light with elliptical polarisation, which is reflected at the testpiece 3, by a rotary movement of the carrier 7, for example in the direction indicated by the arrow 10 in the drawing. The optical layers or films, for example dielectric layers or films, on the polarisation modulating elements, are optically isotropic and homogeneous. However, those layers or films differ from each other in regard to their polarisation properties, for example they are of different thicknesses and/or have different refractive indices. If, during the operation of measuring the properties of the testpiece 3, the polarisation modulating elements are successively moved into the path of the light which is reflected by the testpiece, the state of polarisation of the reflected beam is changed in a different manner, in a stepwise fashion, with the respective state of polarisation produced by a given polarisation modulating element being maintained for as long as the beam reflected by the testpiece 3 impinges on that respective polarisation modulating element. In the case of the embodiment illustrated herein, upon each change from one polarisation modulating element to another, there is a stepwise change in the phase delay between the two perpendicularly mutually oscillating components of the elliptically polarised light which comes from the testpiece 3.

The light which is reflected by the respective polarisation modulating elements on the carrier 7 is then passed through a second polarising means, referred to herein as the analyser 5, and received by a detector which is disposed downstream of the analyser 5, as indicated at 6, the light being received in particular in the form of linearly polarised light. The detector 6 measures the levels of intensity which are associated with the respective polarisation modulating elements 41, 42, 43 and 44. The association between the levels of intensity and the respective modulating elements is effected in a computer 8 which is also fed with the information as to which of the polarisation modulating elements is disposed in the path of the light beam, at the appropriate time. The computer 8 then also provides for interpreting the measurement results produced by the detector.

It should be appreciated that, although the above-described embodiment provides for reflection of the electromagnetic radiation (light) from the light source 1, at the surface of the testpiece 3, it would alternatively be possible for the electromagnetic radiation to be transmitted through the testpiece, with suitable consequential modification of the remainder of the construction, in the appropriate manner. It will also be observed that the carrier 7 of the above-described embodiment has four polarisation modulating elements 41, 42, 43 and 44, which are disposed at spacings from each other and which are successively movable into the path of the light beam by a rotary motion of the carrier 7, with an angle of incidence $>0°$ and $<90°$, but other forms of motion of the polarisation modulating elements may be employed, for example a sliding motion to bring such elements successively into the path of the light beam or an oscillatory movement thereof, and likewise the number of such elements may differ from that illustrated in the specific embodiment. Various other modifications may be made in relation to the arrangement of the polarisation modulating elements which, in the specific embodiment, have their reflective surfaces disposed in parallel relationship to each other, more particularly being disposed in a plane. Furthermore, the assembly illustrated in the drawing is operable to provide for switching the light source on and off in dependence on the movement with which the polarisation modulating elements are successively moved into the path of the light source, whereby the light source is switched on only when a compensating element is in the path of the light beam. It would also be possible to include at least one further optical element in the path of the light beam between the testpiece 3 and at least one of the polariser 2 and the analyser 5, for example at least one additional lens, prism or transparent window. Furthermore, the light source may be such that the wavelength of the light emitted thereby is variable, or a plurality of different wavelengths may be emitted simultaneously. The light source may include for example at least one laser. In addition, as a detail of the illustrated arrangement which may not be immediately apparent therefrom, the angles of incidence of the light on the testpiece surface and the reflecting surface of the respective polarisation modulating element is equal, and the planes of incidence of the beams which are directed on to the testpiece surface and on to the respective reflecting surface are normal to each other. As indicated above, the polariser 2 and the analyser 5 are preferably linear polarisers, the angular settings of which are in perpendicular relationship to each other, along the path of the light beam.

Various other modifications and alterations may be made in the specific embodiment as described and illustrated in the accompanying drawing, without thereby departing from the scope of the present invention.

What is claimed is:

1. In an ellipsometric method for studying physical properties of a testpiece wherein electromagnetic radiation is polarised at a first polarising means, said polarised radiation is brought into operative relationship with the testpiece, the radiation downstream of the testpiece is polarised at a second polarising means, and said radiation is measured and interpreted, the state of polarisation of the radiation being altered between at least one of said first and second polarising means and said testpiece, the improvement which provides that: during the measuring operation at the testpiece the angular positions of the first and second polarising means remain fixed; between at least one of said first and second polarising means and said testpiece at least two discrete, mutually different predetermined states of polarisation of the radiation are produced in a stepwise manner by means of reflection of the radiation at reflecting surfaces having different optical properties, with an angle of incidence $>0°$ and $<90°$; and in regard to each said discrete state of polarisation the respective intensity of the radiation polarised in the second polarising means is measured and interpreted to determine the polarisation properties of the testpiece in a computing means.

2. A method as set forth in claim 1 wherein said polarised radiation is brought into said operative relationship with said testpiece by being reflected thereby.

3. A method as set forth in claim 1 wherein said polarised radiation is brought into said operative relationship with said testpiece by being transmitted therethrough.

4. A method as set forth in claim 1 wherein said physical properties of said testpiece are surface layer properties.

5. An ellipsometric apparatus comprising a radiation source, a first polarising means for receiving and polarising radiation from said source, a station for disposing a testpiece downstream of said first polarising means, a second polarising means disposed downstream of said testpiece station, a detector means disposed downstream of the second polarising means for receiving polarised radiation coming therefrom, and a polarisation modulating means for altering the state of polarisation of the radiation between the said testpiece station and at least one of the first and second polarising means, said polarisation modulating means comprising a plurality of polarisation modulating elements having different discrete predetermined optical properties and disposed at spaced positions from each other, and means for successively moving said polarisation modulating elements into the path of the radiation with an angle of incidence $>0°$ and $<90°$, said polarisation modulating elements being formed as reflecting surface means, each of which has a layer of a homogeneous optically isotropic medium, wherein at least one of the parameters comprising layer thickness and refractive index of the optically isotropic media of said individual polarisation modulating elements differ from each other.

6. Apparatus as set forth in claim 5 wherein each said polarisation modulating element comprises silicon having a polished reflecting surface with a dielectric film thereon as said isotropic medium.

7. Apparatus as set forth in claim 5 wherein said polarisation modulating elements are rotatable about an axis at least substantially normal to the reflective surfaces.

8. Apparatus as set forth in claim 5 wherein the reflective surfaces of said polarisation modulating elements are disposed in parallel relationship to each other.

9. Apparatus as set forth in claim 5 wherein the reflective surfaces of said polarisation modulating elements are disposed in a plane.

10. Apparatus as set forth in claim 5 wherein the reflective surface of each said polarisation modulating element has a single layer thereon.

11. Apparatus as set forth in claim 5 wherein the reflective surface of each said polarisation modulating element has a plurality of coatings thereon.

12. Apparatus as set forth in claim 5 and further including means for switching said light source on and off in independence on the movement with which the polarisation modulating elements are moved into and out of the path of said radiation whereby said light source is switched on only when a said element is in said path.

13. Apparatus as set forth in claim 5 and further including at least one optical element in the path of the radiation between said testpiece and at least one of said first and second polarising means.

14. Apparatus as set forth in claim 13 wherein said optical element includes at least one additional lens.

15. Apparatus as set forth in claim 13 wherein said optical element includes at least one prism.

16. Apparatus as set forth in claim 13 wherein said optical element includes at least one transparent window.

17. Apparatus as set forth in claim 5 wherein said source is adapted to emit light of a variable wavelength.

18. Apparatus as set forth in claim 5 wherein said source is adapted to emit light of different wavelengths simultaneously.

19. Apparatus as set forth in claim 18 wherein said individual wavelengths are dispersed and received by at least two detectors.

20. Apparatus as set forth in claim 5 wherein said source comprises at least one laser.

21. Apparatus as set forth in claim 5 wherein the angle of incidence of the radiation on the testpiece surface and the reflecting surface of the respective polarisation modulating element is substantially the same and the planes of incidence of the beams directed on to the testpiece surface and the respective reflecting surfaces are normal to each other.

22. Apparatus as set forth in claim 5 wherein said first and second polarising means are linear polarising means whose angular positions along said path of the radiation are normal to each other.

23. Apparatus as set forth in claim 5 and comprising four polarisation modulating elements whose polarisation properties are such that the determinant of the matrix which is formed from the four Stokes-vectors which represent the four different states of polarisation of the beams reaching the second polarising means for a testpiece is different from zero.

24. Apparatus as set forth in claim 5 wherein said first and second polarising means are polarising means of reflection type.

25. Apparatus as set forth in claim 5 wherein said angle of incidence is 45 to 80 degrees.

* * * * *